US010022099B2

(12) United States Patent
Tsubota et al.

(10) Patent No.: US 10,022,099 B2
(45) Date of Patent: Jul. 17, 2018

(54) X-RAY IMAGE PICKUP APPARATUS, X-RAY IMAGE PICKUP METHOD, AND X-RAY IMAGE PICKUP APPARATUS MONITORING METHOD

(71) Applicant: Hitachi, Ltd., Tokyo (JP)

(72) Inventors: Yushi Tsubota, Tokyo (JP); Fumito Watanabe, Tokyo (JP); Yasutaka Konno, Tokyo (JP); Shinichi Kojima, Tokyo (JP); Keisuke Yamakawa, Tokyo (JP); Shinji Kurokawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 392 days.

(21) Appl. No.: 14/914,355

(22) PCT Filed: Oct. 22, 2014

(86) PCT No.: PCT/JP2014/078099
§ 371 (c)(1),
(2) Date: Feb. 25, 2016

(87) PCT Pub. No.: WO2015/064446
PCT Pub. Date: May 7, 2015

(65) Prior Publication Data
US 2016/0199018 A1 Jul. 14, 2016

(30) Foreign Application Priority Data
Oct. 31, 2013 (JP) ................................. 2013-227126

(51) Int. Cl.
A61B 6/00 (2006.01)
A61B 6/03 (2006.01)
(Continued)

(52) U.S. Cl.
CPC ............ *A61B 6/5205* (2013.01); *A61B 6/032* (2013.01); *A61B 6/4241* (2013.01); *A61B 6/482* (2013.01);
(Continued)

(58) Field of Classification Search
CPC ....... A61B 6/032; A61B 6/4241; A61B 6/482; A61B 6/5205; A61B 6/582; A61B 6/4035;
(Continued)

(56) References Cited

U.S. PATENT DOCUMENTS 5,040,199 A * 8/1991 Stein ...................... A61B 6/482
378/146
5,570,403 A 10/1996 Yamazaki et al.
(Continued)

FOREIGN PATENT DOCUMENTS

JP 6-296607 A 10/1994
JP 2004-347328 A 12/2004
(Continued)

OTHER PUBLICATIONS

International Search Report of PCT/JP2014/078099.
(Continued)

*Primary Examiner* — Irakli Kiknadze
(74) *Attorney, Agent, or Firm* — Mattingly & Malur, PC

(57) ABSTRACT

A change of X-ray radiation quality due to a material existing between an X-ray source and a detection element is estimated and corrected. Accordingly, deterioration of material discrimination ability in a dual energy imaging method can be prevented. An X-ray imaging apparatus is provided with an inherent filtration calculator configured to use measured data obtained by imaging air at two or more types of different tube voltages to calculate a deviation from a reference radiation quality, as a transmission length (inher-
(Continued)

ent filtration) of a predetermined reference material. A reference-material transmission-length conversion is applied to the measured data according to the dual energy imaging method, thereby calculating the reference material transmission length (inherent filtration). When a subject is imaged, the dual energy imaging is performed by adding the inherent filtration calculated as to each detection element, and this produces an image with the change of radiation quality having been corrected.

15 Claims, 5 Drawing Sheets

(51) Int. Cl.
    *G01N 23/087* (2018.01)
    *G01N 23/046* (2018.01)
(52) U.S. Cl.
    CPC .......... *A61B 6/582* (2013.01); *G01N 23/087* (2013.01); *G01N 23/046* (2013.01)
(58) Field of Classification Search
    CPC ....... A61B 6/405; A61B 6/027; A61B 6/4042; A61B 6/4007; A61B 6/4021; A61B 6/4028; A61B 6/4233; A61B 6/502; A61B 6/505; A61B 6/583; A61B 6/00; A61B 6/06; A61B 6/4014; A61B 6/05; A61B 6/4085; A61B 6/466; A61B 6/488; A61B 6/542; A61B 6/504; A61B 6/481; A61B 6/4208; G01N 23/046; G01N 23/087; A01G 9/227; E04F 10/0607; E04F 10/0644; E04F 10/0681
    USPC ................................ 378/4, 16, 19, 156–158
    See application file for complete search history.

(56) References Cited

U.S. PATENT DOCUMENTS

| | | | | |
|---|---|---|---|---|
| 7,046,756 | B2* | 5/2006 | Hoffman | A61B 6/032 378/158 |
| 8,218,728 | B2* | 7/2012 | Karch | A61B 6/032 378/156 |
| 8,571,178 | B2* | 10/2013 | Sendai | A61B 6/4042 378/157 |
| 2004/0136491 | A1 | 7/2004 | Iatrou et al. | |
| 2009/0122952 | A1 | 5/2009 | Nishide et al. | |

FOREIGN PATENT DOCUMENTS

| | | |
|---|---|---|
| JP | 2005-533564 A | 11/2005 |
| JP | 2009-112627 A | 5/2009 |

OTHER PUBLICATIONS

International Preliminary Report on Patentability received in corresponding International Application No. PCT/JP2014/078099 dated May 12, 2016.

* cited by examiner

X-RAY IMAGE PICKUP APPARATUS, X-RAY IMAGE PICKUP METHOD, AND X-RAY IMAGE PICKUP APPARATUS MONITORING METHOD

TECHNICAL FIELD

The present invention relates to a dual energy imaging method in an X-ray imaging apparatus.

BACKGROUND ART

As an imaging method that uses an X-ray CT (Computed Tomography) apparatus, there is a dual energy imaging method (Patent Document 1). The dual energy imaging method is a technique utilizing a property (energy dependence) that a mass attenuation coefficient varies depending on a material and X-ray energy, and an image of an identical subject is taken using two different types of tube voltage, i.e., different energy distributions, thereby obtaining information regarding a material composition of the subject.

PRIOR ART DOCUMENT

Patent Document

Patent Document 1
Japanese Unexamined Patent Application Publication (Translation of PCT Application) No 2005-533564

DISCLOSURE OF THE INVENTION

Problems to be Solved by the Invention

In the dual energy imaging method as described in the patent document 1, a slight design tolerance, or the like, of a material existing between an X-ray focused point and a detection element may change a radiation quality of the X-rays, and it may induce deterioration of material discrimination ability. Specific examples of the material that may change the radiation quality of the X-rays may be materials of an X-ray tube, a collimator, a beam compensation filter, and a scatter removal grid, and an arrangement error or a dimension error of those materials may cause the change of radiation quality. A heel effect on the tube anode may also change the radiation quality.

An object of the present invention is to provide a means that corrects the change of radiation quality as described above, without requiring design accuracy excessively.

Means for Solving the Problems

In order to solve the problem as described above, according to the present invention, air (including no subject) is imaged at two different types of tube voltage, and a reference-material transmission-length conversion is applied according to the dual energy imaging method. Then, a change of radiation quality (a deviation from a reference radiation quality) attributed to the imaging apparatus, is calculated as a transmission length, that is, inherent filtration, of a predetermined reference material (a specific reference material), as to each detection element.

In other words, the X-ray imaging apparatus of the present invention is provided with; an X-ray source configured to generate plural X-rays having different energy, an X-ray detector having plural detection elements and being disposed in a manner opposed to the X-ray source, a rotary table configured to rotate with supporting the X-ray source and the X-ray detector, and an arithmetic unit that calculates information relating to materials existing between the X-ray source and the X-ray detector by using measured data detected by the X-ray detector under conditions of different X-ray distributions produced by the X-ray source, wherein the arithmetic unit is provided with an inherent filtration calculator configured to use the measured data detected by the X-ray detector when no subject exists between the X-ray source and the X-ray detector, with respect to each of conditions of different X-ray energy distributions, to calculate a transmission length (inherent filtration) of arbitrary reference material as to each of the detection elements of the X-ray detector.

An X-ray imaging method of the present invention is a method of imaging a subject in plural types of energy distributions for obtaining plural types of subject projection data, imaging in advance without any subject, in different plural types of energy distributions, calculating a change of radiation quality of X-rays incident on each detection element, as a transmission length of any material, the number of which is equal to or less than the number of the types of energy distributions, on the basis of air projection data obtained by imaging in the plural types of energy distributions, and creating an image with the change of radiation quality having been corrected by using the calculated change of radiation quality and the plural types of subject projection data.

A monitoring method of the X-ray imaging apparatus of the present invention, the apparatus being provided with an X-ray detector having plural detection elements, is a method of imaging in advance without any subject in different plural types of energy distributions, calculating from the plural types of air projection data, a change of radiation quality of X-rays incident on each of the detection elements as a transmission length of any material, the number of which is equal to or less than the number of types of energy distributions, and displaying a difference in radiation quality properties between adjacent elements or between adjacent modules, by using the transmission length thus obtained.

Advantages of the Invention

A deviation from the reference radiation quality is obtained, which is represented by a transmission length (inherent filtration) of a predetermined reference material, and when imaging a subject, for instance, the dual energy imaging method is performed, considering the inherent filtration of each detection element, thereby enabling correction of the change of radiation quality. Accordingly, it is possible to provide a high quality CT image with the change of radiation quality having been corrected, without excessively requiring design accuracy. In addition, by comparing inherent filtration values being calculated as to each detection element, a defective detection element can be detected.

BEST MODE FOR CARRYING OUT THE INVENTION

Figure 1:
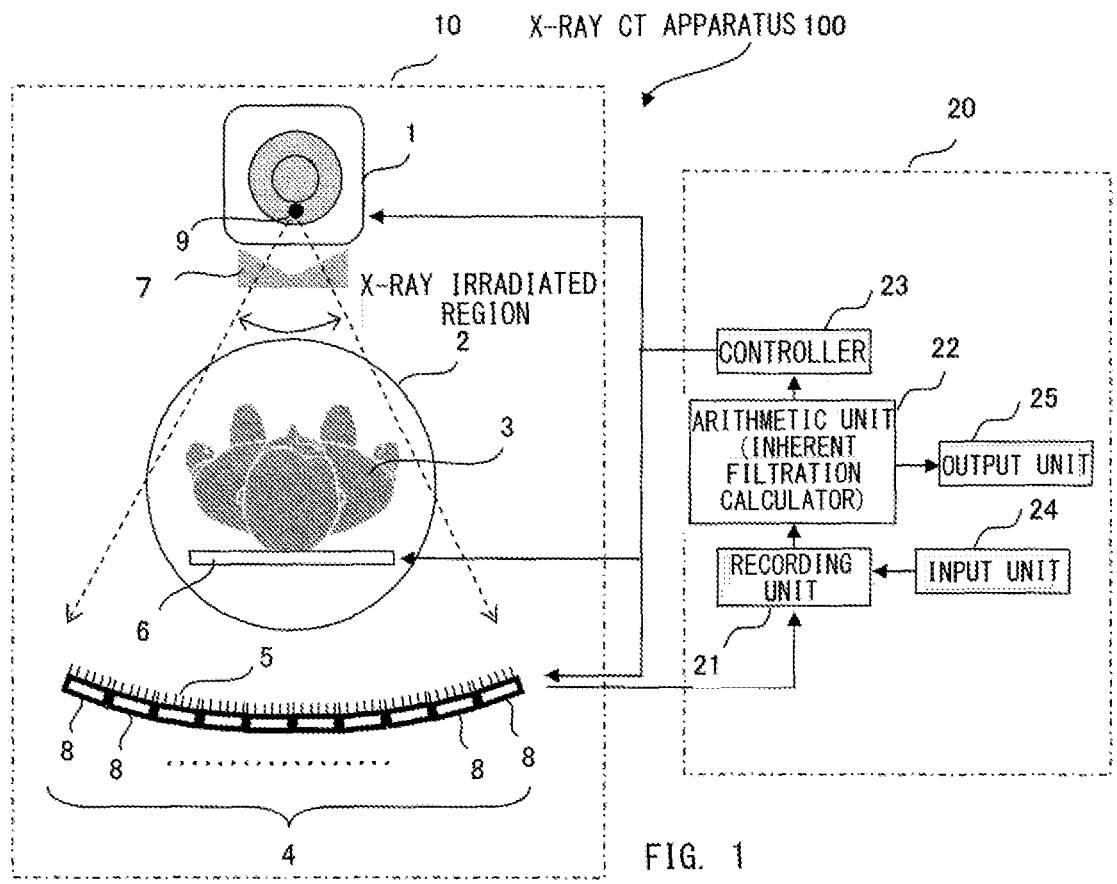
FIG. 1 is an overall block diagram including a schematic structure of an X-ray CT apparatus viewed in a body axis direction, according to an embodiment of the present invention.

Preferred embodiments of an X-ray CT apparatus according to the present invention will now be described, with reference to the accompanying drawings. FIG. 1 illustrates an overall configuration of the X-ray CT apparatus that is described commonly in each embodiment. The X-ray imaging apparatus of the present embodiment is provided with an X-ray source 1 configured to generate plural X-rays with various energy, an X-ray detector 4 including plural detection elements, being arranged in a manner opposed to the X-ray source, a rotary plate configured to rotate with supporting the X-ray source and the X-ray detector, and an arithmetic unit 22 configured to calculate information as to a material existing between the X-ray source and the X-ray detector by using measured data detected by the X-ray detector under each of conditions of different X-ray energy distributions generated by the X-ray source, wherein the arithmetic unit is further provided with an inherent filtration calculator 223 configured to calculate a transmission length of a specific reference material to obtain inherent filtration, as to each detection element of the X-ray detector, by using the measured data detected by the X-ray detector when no subject exists between the X-ray source and the X-ray detector, with respect to each of the plural conditions of different X-ray energy.

The inherent filtration calculator uses the measured data detected by the X-ray detector and theoretical value of an output from the X-ray detector obtained by calculation as to the specific reference material, to calculate the transmission length of the reference material as to each detection element. The transmission length of the specific reference material, obtained as to each detection element, represents a change of a radiation quality (radiation quality change) attributed to the X-ray CT apparatus, and it is used for creating an image of the subject and for determining abnormality in each of the detection elements.

The X-ray CT apparatus 100 as shown in FIG. 1 roughly includes an imaging part 10 where the subject 3 is placed, and an operating part 20 for an operator to manipulate and control the apparatus. The imaging part 10 includes mainly, a scanner unit (rotary plate) accommodated in a gantry not illustrated, an X-ray tube 1 serving as the X-ray source, the X-ray detector 4, and a bed unit 6 on which the subject 3 is placed. At the center of the gantry, there is formed an opening 2 into which a top board of the bed unit 6 is moved, placing the subject 3 thereon, and the scanner unit is supported by the gantry in a rotatable manner, using the center of the opening 2 as a rotation axis. With this configuration, it is possible to take an image of the subject 3 within the opening 2, by rotary imaging.

The X-ray tube 1 serving as the X-ray source generates X-rays from the X-ray focused point 9 of a finite size within the X-ray tube 1. The X-ray tube 1 is connected to a power supply unit not illustrated, and in the present embodiment, there is provided a configuration that enables multi-energy imaging. By way of example, either of plural types of tube voltage is selectively supplied from the power supply unit, whereby plural types of X-rays having different energy distributions are generated. The tube voltage may include various types, such as 80 kV, 120 kV, 140 kV, and 160 kV. Alternatively, it is possible to provide plural X-ray tubes 1 which generate plural types of X-rays, respectively.

The X-ray detector 4 is disposed at the position that is opposed to the X-ray tube 1, placing the subject 3 therebetween. The X-ray detector 4 includes plural detection elements being arranged in an arc form about the X-ray focused point. In addition to the arrangement in one-dimensional array along the arc form, they may be arranged along the direction of the rotation axis of the scanner unit. The X-ray detector 4 may be divided into detector modules 8, each made up of a predetermined number of detection elements, and the detector modules 8 are arranged in an arc form or in a flat panel form, about the X-ray focused point 9. On the side of the detector module 8 facing the X-ray tube 1, a scatter removal grid 5 is provided, so as to remove scattered X-rays caused by the subject 3, or the like. A beam compensation filter 7 is provided between the subject 3 and the X-ray tube 1, so that the X-rays being detected have a homogeneous radiation quality (energy spectrum) and intensity.

The operating part 20 is a unit configured for the user to input various conditions and data necessary for imaging and to control the imaging by the X-ray CT apparatus 100, and it is provided with a recording unit 21 such as a memory and a hard disk drive, an arithmetic unit 22 configured to perform operations such as an image processing operation, a controller 23 configured to control imaging, an input unit 24 such as a mouse and a keyboard, and an output unit 25 such as a monitor. Functions of the arithmetic unit 22 and the controller 23 are implemented through execution of programs incorporated in advance in a CPU (Central Processing Unit) and the like, or read from an external storage. It should be noted that hardware such as ASIC (Application Specific Integrated Circuit) and FPGA (Field Programmable Gate Array), and a publicly known electrical circuit may implement a part of or all of the functions of the arithmetic unit.

The controller 23 drives and controls an X-ray power supply and the scanner unit on the basis of a scanning condition that is provided by the user through the input unit 24, whereby the imaging is performed. The recording unit 21 records a large amount of projection data obtained by rotary imaging, and the arithmetic unit 22 executes an image processing operation on the data, which is displayed on the output unit 25, in the form of information such as a tomographic image of the subject 3.

The controller 23 controls the X-ray tube 1 and the X-ray detector 4 to perform multi-energy imaging. There are various methods to obtain a projection data set of the subject, according to the multi-energy imaging, that is, on the basis of different energy distributions, and controls are various depending on those methods. Byway of example, dual energy imaging, which is one mode of the multi-energy imaging, includes, a double-rotation system configured to perform imaging twice using different tube voltage, a high-speed tube voltage switching system configured to switch the tube voltage at high speed during one rotation, a two-layered detector system configured to have two layers for measuring X-rays of a low energy distribution in the upper layer and measuring X-rays of a high energy distribution in the lower layer, a double tube system configured to have two pairs of a tube and a detector within a gantry, to perform imaging with setting of tube voltage having values different between each of the tubes, a photon-counting system configured to measure X-rays in photon units so as to measure the X-ray energy, and a method of arranging detection elements with different energy sensitivities in an alternate manner on a two-dimensional array surface.

Any of the methods described above may be employed in the present embodiment, and the aforementioned X-ray tube 1 and X-ray detector 4 are provided with a configuration in conformity with the system being employed.

The imaging processing operation performed by the arithmetic unit 22 may include an image reconstruction operation using the measured data, and in addition, further includes various correction processes, such as intensity correction (reference correction), sensitivity correction of the detection element (air correction), and a logarithmic transformation. Furthermore, the imaging processing operation includes an operation regarding X-ray transmission length, i.e., inherent filtration of a specific reference material, which will be described below. A part in the arithmetic unit 22 for performing this operation of inherent filtration is referred to as an inherent filtration calculator 223. A table and the like, used for the operation by the arithmetic unit 22 are stored in a storage part that is provided in the recording unit 21 or in the arithmetic unit 22.

In view of the configuration of the X-ray CT apparatus described above, each embodiment mainly characterized in the functions of the arithmetic unit 22 will now be described.

First Embodiment

An X-ray CT apparatus of the present embodiment features that an arithmetic unit 22 which uses measured data acquired by multi-energy imaging to perform various operations including image reconstruction, calculates inherent filtration, i.e., a transmission length of a specific reference material, obtained as to each detection element, and utilizes the calculation result to generate an image of the subject.

In other words, the X-ray CT apparatus of the present embodiment includes, a storage part 222 configured to store in the form of a conversion table, dependence of an X-ray detector output on a predetermined material constituting the subject, with respect to each condition of different X-ray energy distributions, and an image generator 221 configured to use a measured value detected by the X-ray detector when a subject 3 exists between the X-ray source 1 and the X-ray detector 4, and a theoretical value calculated from a transmission length of a material constituting the subject, and the conversion table being a subject transmission length conversion table, stored in the storage part, so as to create an image of the subject. The subject transmission length conversion table is corrected with the use of the inherent filtration that is calculated by the inherent filtration calculator 223.

Figure 2:
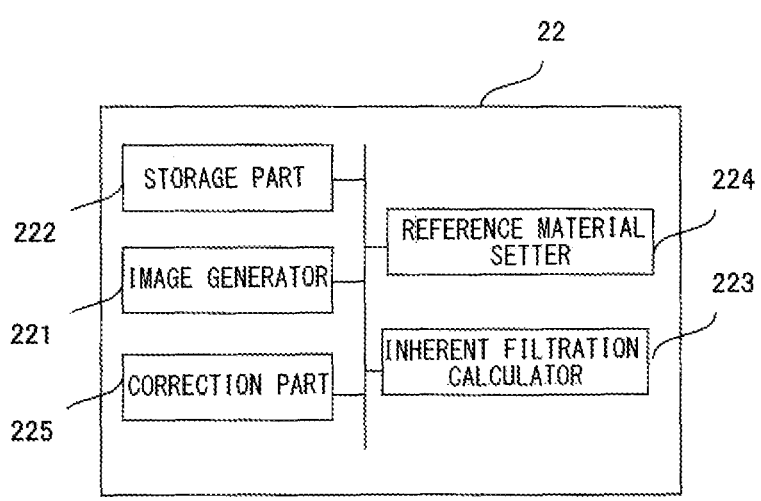
FIG. 2 is a functional block diagram showing an arithmetic unit of the X-ray CT apparatus as shown in FIG. 1.

FIG. 2 is a functional block diagram showing the arithmetic unit 22. As illustrated, the arithmetic unit 22 is provided with an image generator 221 configured to perform an arithmetic operation using the measured data for creating an image such as a tomographic image of the subject using measured data, a storage part 222 configured to store a conversion table necessary for creating an image by multi-energy imaging, an inherent filtration calculator 223 configured to calculate a radiation quality change attributed to the apparatus, as an inherent filtration value of a specific reference material, a reference material setter 224 configured to set the specific reference material used in the inherent filtration calculator 223, and a correction part 225 configured to perform correction such as air correction and intensity correction on the measured data by using the inherent filtration value of the reference material, calculated by the inherent filtration calculator 223. It should be noted that the recording unit 21 that records the projection data acquired by imaging, may also function as the storage part 222.

Figure 3:
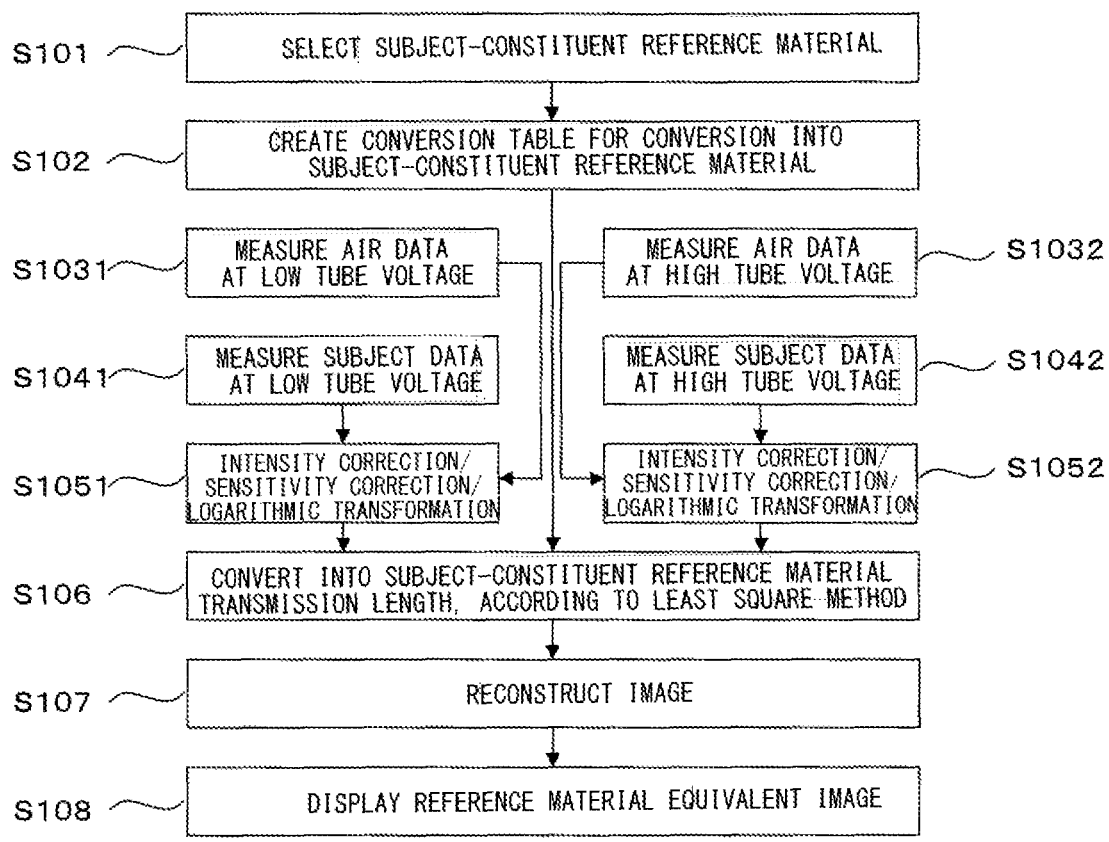
FIG. 3 illustrates one example of processing procedure of a dual energy imaging method employed in a first embodiment.

Now, there will be described an operation of the X-ray CT apparatus having the aforementioned configuration according to the present embodiment. The X-ray CT apparatus according to the present embodiment performs multi-energy imaging which uses different N (N is an integer equal to or larger than 2) types of energy distributions, so as to distinguish materials constituting the subject from one another. In the following, there will be described an example of dual energy imaging that uses two types of tube voltage; low tube voltage (e.g., 80 kV) and high tube voltage (e.g., 140 kV). FIG. 3 is a flowchart illustrating a process of the dual energy imaging method being a reference material decomposition type, which is a typical example of the dual energy imaging employed by the present embodiment. The image generator 221 mainly executes this process.

In the typical dual energy imaging as shown in FIG. 3, firstly, a material whose contrast is required to be intensified is selected as a reference material constituting the subject, in response to a user's purpose of imaging (S101). By way of example, in a contrast examination, in the case where the contrast of an iodine contrast agent (I) is required to be intensified against soft tissue or water ($H_2O$), water and iodine contrast agent are selected. When imaging is performed in N types of energy distributions, N types of reference materials are selectable.

Next, dependence of an output I on the reference material transmission length is calculated, as to each of two types of the tube voltage (low tube voltage and high tube voltage), and the result is stored in a conversion table (subject transmission length conversion table) (S102). In practice, the dependence on the reference material transmission length, of the output J after subjected to the logarithmic transformation described below is provided in the form of the conversion table.

The dependence of the output I on the reference material transmission length ($s_i$) can be calculated as the following.

In general, the output I at each detection element is represented by the formula 1:

[Formula 1]

$$I = \int S(\varepsilon)\varepsilon\eta(\varepsilon)\mathrm{Exp}\left[-\mu(\varepsilon, Z(s), s)\rho(s)ds\right]d\varepsilon \quad (1)$$

where S is X-ray generation spectrum, $\varepsilon$ is X-ray energy, $\eta$ is detection efficiency, $\mu$ is a mass attenuation coefficient, Z is the atomic number, s is an X-ray path, and $\rho$ is material density. The mass attenuation coefficient can be broken down as shown in the formula 2, by using three reference materials, including the water and iodine contrast agent constituting the subject, which are selected in the process S101, adding air (AIR) thereto. Then, this is substituted into the formula 1, thereby obtaining the formula 3. For ease of explanation, the detection efficiency $\eta$ is assumed as 1. In the formula, the subscripts "AIR", "$H_2O$", "I" represent values, respectively relating to the reference materials; air, water, and iodine.

[Formula 2]

$$\int \mu(\varepsilon, Z(s), s)\rho(s)ds \approx \mu_{AIR}\rho_{AIR}s_{AIR} + \mu_{H2O}\rho_{H2O}s_{H2O} + \mu_I\rho_I s_I \quad (2)$$

[Formula 3]

$$I(s_{AIR}, s_{H2O}, s_I) = \int S(\varepsilon)\varepsilon \text{Exp}[-\mu_{AIR}\rho_{AIR}s_{AIR} - \mu_{H2O}\rho_{H2O}s_{H2O} - \mu_I\rho_I s_I]d\varepsilon \quad (3)$$

When theoretical values are substituted into the formula 3, assuming that the mass attenuation coefficient $\mu_i$ and the density $\rho_i$ of the reference material constituting the subject (hereinafter, indicated by the subscript "i") and incident spectrum S are known values, the detection element output I can be considered as a function of the transmission length $s_i$ only. Since the length from the X-ray focused point to each of the detection elements is kept constant ($\Sigma_i s_i$=const.) while the imaging is performed, the output I becomes a function substantially having two variables. In other words, the formula 3 expresses that the output I has the dependence on the reference material transmission length ($s_i$). It should be noted that in the example here, a representative value is used as the density, and variations of the density are tentatively considered to be replaced by variations of length.

The dependence of the output I on the reference material transmission length ($s_i$) obtained by the formula 3, is used as a conversion table (subject transmission length conversion table) for the conversion to the reference materials constituting the subject in the dual energy imaging. In the present embodiment, however, this conversion table is replaced by a conversion table that has been subjected to a radiation quality correction in the process described in the following.

Next, in order to correct sensitivity variations in each of the detection elements, an output of the detector is measured in the state where there is no subject under the conditions of both low tube voltage and high tube voltage (S1031 and S1032). The data items being obtained are assumed as $I_{0L}$ and $I_{0H}$. Those data items are referred to as "air data" in general. The storage part 222 stores the air data.

Next, the subject is measured under the conditions of both low tube voltage and high tube voltage (S1041 and S1042). The obtained measured data items are represented as $I_L$ and $I_H$.

Using the formulas 4 and 5, the measured data items are subjected to intensity correction (reference correction) of X-ray radiation, sensitivity correction (air correction) of the detection element, and logarithmic transformation (S1051 and S1052) (correction part 225). An output value after the logarithmic transformation is performed is represented as J.

[Formula 4]

$$J_L = -\text{Gain} \times \text{Log}_{10}\left(\frac{I_L}{I_{0L}} \frac{I_{0L}^{ref}}{I_L^{ref}}\right) \quad (4)$$

[Formula 5]

$$J_H = -\text{Gain} \times \text{Log}_{10}\left(\frac{I_H}{I_{0H}} \frac{I_{0H}^{ref}}{I_H^{ref}}\right) \quad (5)$$

In the formulas, Gain represents an appropriate constant, and the subscript "ref" represents a representative output (reference data) of each measured data. As the representative output, an output of the element (reference element) at the end of the detector 4 may be used, so as not to be covered by a shade of the subject or scattered radiation.

Next, according to the formula 6, the transmission length $s_i$ of the reference material constituting the subject is obtained from the output of the measured value (S106). The formula 6 expresses a process to retrieve from the conversion table, a combination of the lengths $s_i$ minimizing a square of the difference between the measured values $J_L$ and $J_H$, and the theoretical values $J_L^{ideal}$ and $J_H^{ideal}$ obtained by calculation, and this process is referred to as a transmission length conversion.

[Formula 6]

$$\min \chi^2(s_i), \chi^2(s_i) \equiv (J_L - J_L^{ideal}(s_i))^2 + (J_H - J_H^{ideal}(s_i))^2 \quad (6)$$

The reference material transmission length $s_i$ of the material constituting the subject, which is obtained in the process S106, is converted into a dimension of density×length according to the formula 7, and an image is reconstructed from each result (S107), thereby obtaining an image equivalent to each reference material (S108). In the example as described above, there are obtained images equivalent to soft tissue and contrast agent, or an image equivalent to water and an image equivalent to the contrast agent.

[Formula 7]

$$J_i = \text{Gain}_i \times \rho_i s_i \quad (7)$$

According to this method, each reference material can be separated clearly in the form of images, and since the image is created taking energy into account, it is possible to remove artifact that is caused by beam hardening. However, influences of slight design tolerance of a material existing between the X-ray focused point and the detection element, varying in each apparatus, are not reflected on the theoretical values $J_L^{ideal}$ and $J_H^{ideal}$ of the output value used in the formula 6, and thus there is a possibility that a radiation quality change due to those design tolerance, and the like, may lower the material discrimination ability in the reference material image. In the present embodiment, in order to prevent degradation of material discrimination ability due to the radiation quality change, measured data (air data) measured in the state where there is no subject, is used to estimate a radiation quality change caused by the design tolerance of the apparatus, and the like, and correction is performed with the use of the obtained result.

Figure 4:
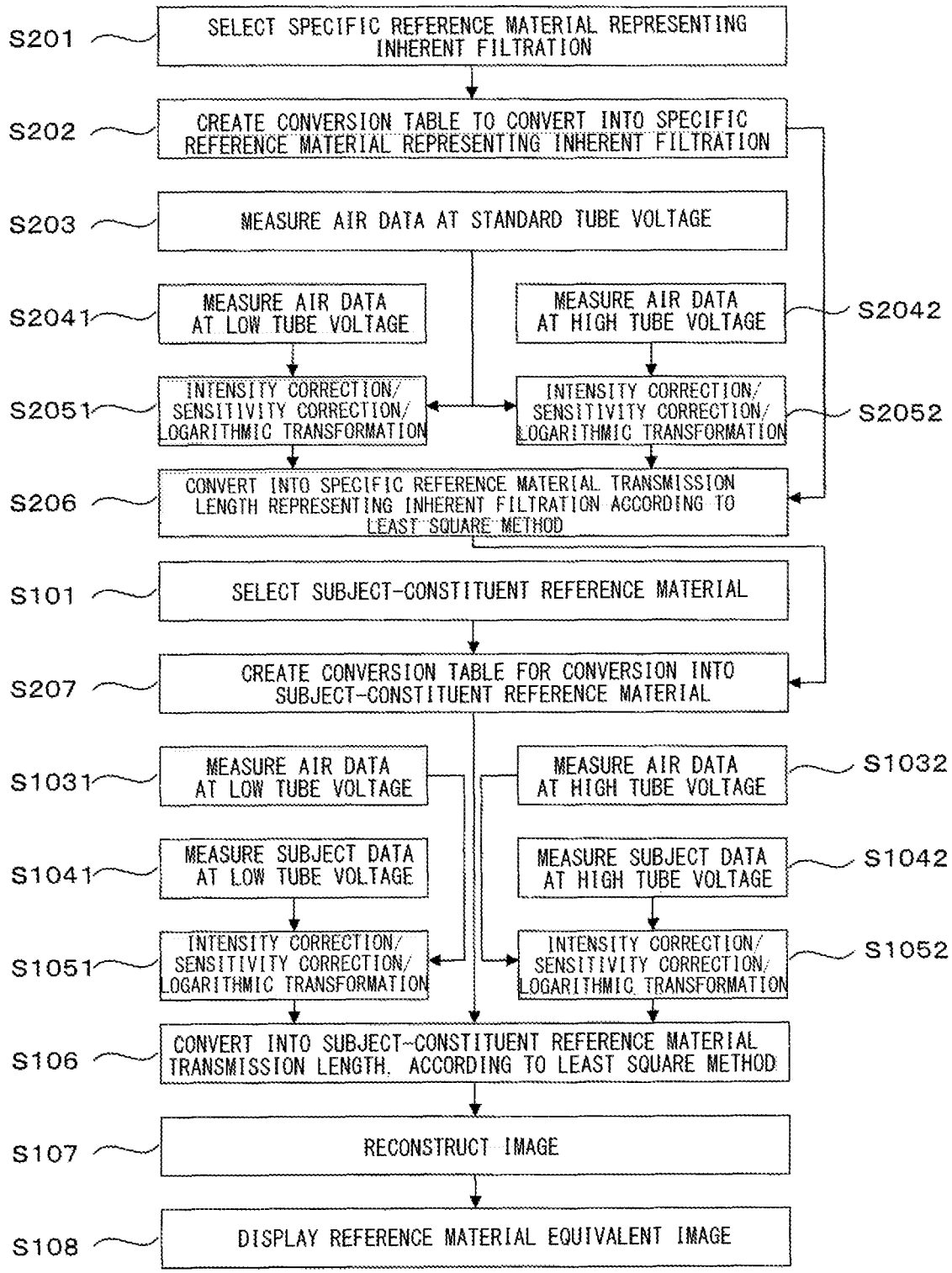
FIG. 4 is an example of flowchart of data processing according to the first embodiment.

A process will now be described, for estimating and correcting the radiation quality change with respect to each detection element, by using air data. FIG. 4 is an overall flowchart showing the present embodiment where the estimation and correction process as described above is added to the flowchart of the image generating process as shown in FIG. 3. The processes with the same functions as those in FIG. 3 are labeled with the same reference numerals, and they will not be redundantly explained. As shown in FIG. 4, the processes S201 to S207 are added to this flowchart. Those processes are implemented mainly by the inherent filtration calculator 223.

Here, there will be described the case where the air data measured in three different types of energy distributions is taken as an example. The air data to be used may be obtained by the measurement in M different types of energy distributions (M is an integer two or more) and M=3 is not the only example.

Firstly, a reference material is selected to represent the change of radiation quality as inherent filtration (S201). In the present example, in order to distinguish from the reference material selected in the image generation process S101, the reference material used here is referred to as a specific reference material. The specific reference material is provided to represent the change of radiation quality as inherent filtration thereof, and any material is selectable. By way of example, it is possible to select a material such as aluminum (Al) and copper (Cu), which may be used to make a beam compensation filter. The material may be a virtual material having an arbitrary mass attenuation coefficient with optional energy dependence and optional density. Following description will be provided assuming that Al and Cu are used as the specific reference materials.

When imaging is performed in M types of energy distributions (M is an integer two or more), (M−1) types of specific reference materials are selectable. A user is not necessarily required to perform this selection process, and it may be preset in the reference material setter 224 by default. Alternatively, the user may provide or select the materials via the input unit 24 so as to provide them in the reference material setter 224.

Next, similar to the process S102 in the image generation, a conversion table for the specific reference material transmission length representing inherent filtration and a detector output is created and stored (S202). For this step, firstly, as shown in the formula 8, the mass attenuation coefficient is broken down, by using three specific reference materials, i.e., the materials indicating the inherent filtration selected in the process S201 and the air (AIR) added thereto. Also in this formula, the subscripts "AIR", "Al", and "Cu" represent values respectively relating to the specific reference materials; air, Al, and Cu. This formula is substituted into the aforementioned formula 1, assuming the detection efficiency η as 1, and the formula 9 is obtained accordingly.

[Formula 8]

$$\int \mu(\varepsilon, Z)\rho(s)ds \approx \mu_{AIR}\rho_{AIR}s_{AIR} + \mu_{Al}\rho_{Al}s_{Al} + \mu_{Cu}\rho_{Cu}s_{Cu} \quad (8)$$

[Formula 9]

$$I(s_{AIR}, s_{Al}, s_{Cu}) = \int S(\varepsilon)\varepsilon \mathrm{Exp}[-\mu_{AIR}\rho_{AIR}s_{AIR} - \mu_{Al}\rho_{Al}s_{Al} - \mu_{Cu}\rho_{Cu}s_{Cu}]d\varepsilon \quad (9)$$

In the following, the reference material (specific reference material) to represent the inherent filtration, is expressed with the subscript j, so as to be distinguished from the reference material that represents the subject (the material constituting the subject, being selected in accordance with a purpose of imaging). Also in this case, the detection element output I or the output J after the logarithmic transformation is performed may be considered as a function of the specific reference material transmission length $s_j$ only, which represents the inherent filtration. Accordingly, similar to the process of S102, a dependence of the output on $s_j$ (a specific reference material transmission length representing the inherent filtration) can be calculated in advance according to the formula 9, and the result is stored in the form of the conversion table. Also in this case, the sum of the transmission length of the specific reference materials is constant ($\Sigma_j s_j$=const.), and thus it is possible to regard the output I or J as a function having two variables, substantially.

Next, in order to correct sensitivity variations in each of the detection elements, the air data at the standard tube voltage (e.g., 120 kV) is measured (S203). Data being obtained is assumed as $I_{OS}$. In addition, air data is measured at two types of tube voltage (low tube voltage and high tube voltage) (e.g., 80 kV, and 140 kV) different from the standard tube voltage (S2041 and S2042). The data items being obtained are assumed as $I_{OL}$ and $I_{OH}$. Since the air data does not depend on a projection angle, averaging of views may be performed as required.

Next, according to the formulas 10 and 11, intensity correction (reference correction) according to one representative element, and sensitivity correction (air correction) according to the standard air data $I_{OS}$, and logarithmic transformation are performed (S2051 and S2052).

[Formula 10]

$$J_{OL} = -\mathrm{Gain} \times \mathrm{Log}_{10}\left(\frac{I_{OL}}{I_{OS}} \frac{I_{OS}^{ref}}{I_{OL}^{ref}}\right) \quad (10)$$

[Formula 11]

$$J_{OH} = -\mathrm{Gain} \times \mathrm{Log}_{10}\left(\frac{I_{OH}}{I_{OS}} \frac{I_{OS}^{ref}}{I_{OH}^{ref}}\right) \quad (11)$$

As the reference element in the formulas 10 and 11, it is desirable to select an element that may minimize the change of radiation quality. By way of example, the element to be selected may be placed at a slice on the side of electron source (cathode) with little change of radiation quality due to a heel effect, and corresponding to a part where the beam compensation filter is thinnest. The transmission length $s_j$ of the specific reference material representing the inherent filtration is obtained from those measured value outputs $J_{OL}$ and $J_{OH}$, and the theoretical values $J_{OL}^{ideal}$ and $J_{OH}^{ideal}$ obtained by calculation. Specifically, by using the transmission length conversion according to the least square method as expressed by the formula 12, a combination of $s_j$ is searched out from the conversion table created in S202 (S206).

[Formula 12]

$$\min \chi^2(s_j), \chi^2(s_j) \equiv (J_{OL} - J_{OL}^{ideal}(s_j))^2 + (J_{OH} - J_{OH}^{ideal}(s_j))^2 \quad (12)$$

When there are M types of air data being imaged at different tube voltage, one of those data items is assumed as standard air data for sensitivity correction. Using a ratio of the standard air data to the remaining (M−1) types of air data, similar to the aforementioned method, the specific reference material transmission length $s_j$ to represent M types of inherent filtration can be estimated.

Next, according to the radiation quality change estimated in the aforementioned process S206, a property of the radiation quality that is different with respect to each detection element is corrected (S207). Specifically, in the process of S102 of the dual energy imaging method as shown in FIG. 3, when the conversion table ($J_L^{ideal}(s_i)$, $J_H^{ideal}(s_i)$) (subject transmission length conversion table) is created for the conversion into the reference material constituting the subject, it is sufficient to perform calculation by replacing the formula 3 by the formula 13. In this case, however, it is assumed that the transmission length of air is not included in $s_j$.

[Formula 13]

$$I(s_i) = \int S(\varepsilon)\varepsilon \eta(\varepsilon) \mathrm{Exp}\left[-\sum_i^{N+1} \mu_i \rho_i s_i - \sum_j^{M-1} \mu_j \rho_j s_j\right] d\varepsilon \quad (13)$$

Since the transmission length of the specific reference material $s_j$ representing the inherent filtration is different as to each detection element, $J_L^{ideal}(s_i)$ and $J_H^{ideal}(s_i)$ are also required to be calculated as to each detection element.

Details of other processing, i.e., the processes of selecting the reference material constituting the subject (S101) and the processes after creating the subject transmission length conversion table (S1031 to S1051, S1032 to S1052, S106 to S108) are identical to the processes labeled with the same reference numerals in FIG. 3, and they will not be redundantly explained. The air data measurement process S2041 may be integrated with the process S1031 and the process S2042 may be integrated with the process S1032, if the tube voltage is identical. That is, in the case where the air data is measured in the process S2041 and S2042 at the same two types of tube voltage as the two types of tube voltage when imaging the subject, for instance, the air data measurement processes S1031 and S1032 for imaging the subject may be skipped. In this case, air data measured in the processes S2041 and S2042 and stored in the storage part 222 can be used in the next correction processes S1051 and S1052.

FIGS. 3 and 4 show the embodiment that two types of voltage; low tube voltage and high tube voltage, are used, and the number of different energy distributions M used in measuring the air data, and the number of different energy distributions N used in imaging the subject, have the relation of M=N=2. However, the number of different energy distributions N used in imaging the subject and the number of different energy distributions M used in measuring the air data may be provided independently, and those numbers may be identical or not identical.

In the process S108, it has been shown the case where a reference material equivalent image is obtained. It is further possible to obtain a virtual standard tube voltage image, a virtual monochromatic X-ray image, an effective atomic number image, an electron density image, an interaction intensified image, and the like, on the basis of the same information (the transmission length of the specific reference material, representing the inherent filtration obtained in the process S206, and the transmission length conversion table obtained in the process S207).

According to the imaging method of the present embodiment, a radiation quality change attributed to the apparatus is obtained as inherent filtration of a predetermined reference material (specific reference material) and the calculation of the transmission length of the reference material constituting the subject is corrected, by use of the inherent filtration above. Therefore, the transmission length of the reference material can be obtained more accurately, thereby enhancing an image quality of the reference material equivalent image and the virtual monochromatic image. Consequently, without excessively requiring design accuracy of the apparatus, it is possible to easily reduce an influence of the radiation quality change due to an arrangement error or a dimension error of the X-ray tube, collimator, beam compensation filter, or scatter removal grid device, and the heel effect, whereby a high quality image can be obtained.

Second Embodiment

An X-ray CT apparatus of the present embodiment features that by using inherent filtration calculated by the inherent filtration calculator for each detector, a detection element with the least change of radiation quality is estimated, and this detection element is used as a reference detection element for correcting intensity.

In other words, in the X-ray CT apparatus of the present embodiment, the arithmetic unit 22 is provided with a correction part 225 that corrects intensity, using one element among plural detection elements as a reference element. The arithmetic unit uses the transmission length of the specific reference material calculated by the inherent filtration calculator 223 for each detection element, to select a detection element where a deviation from the reference radiation quality is minimum, and the correction part performs the intensity correction using thus selected detection element as the reference element.

Since the functions of the X-ray CT apparatus (arithmetic unit 22) of the present embodiment may be implemented by each of the components in the functional block diagram of the first embodiment as shown in FIG. 2, those components in FIG. 2 will now be quoted as required in the following, and each component will not be described redundantly.

Figure 5:
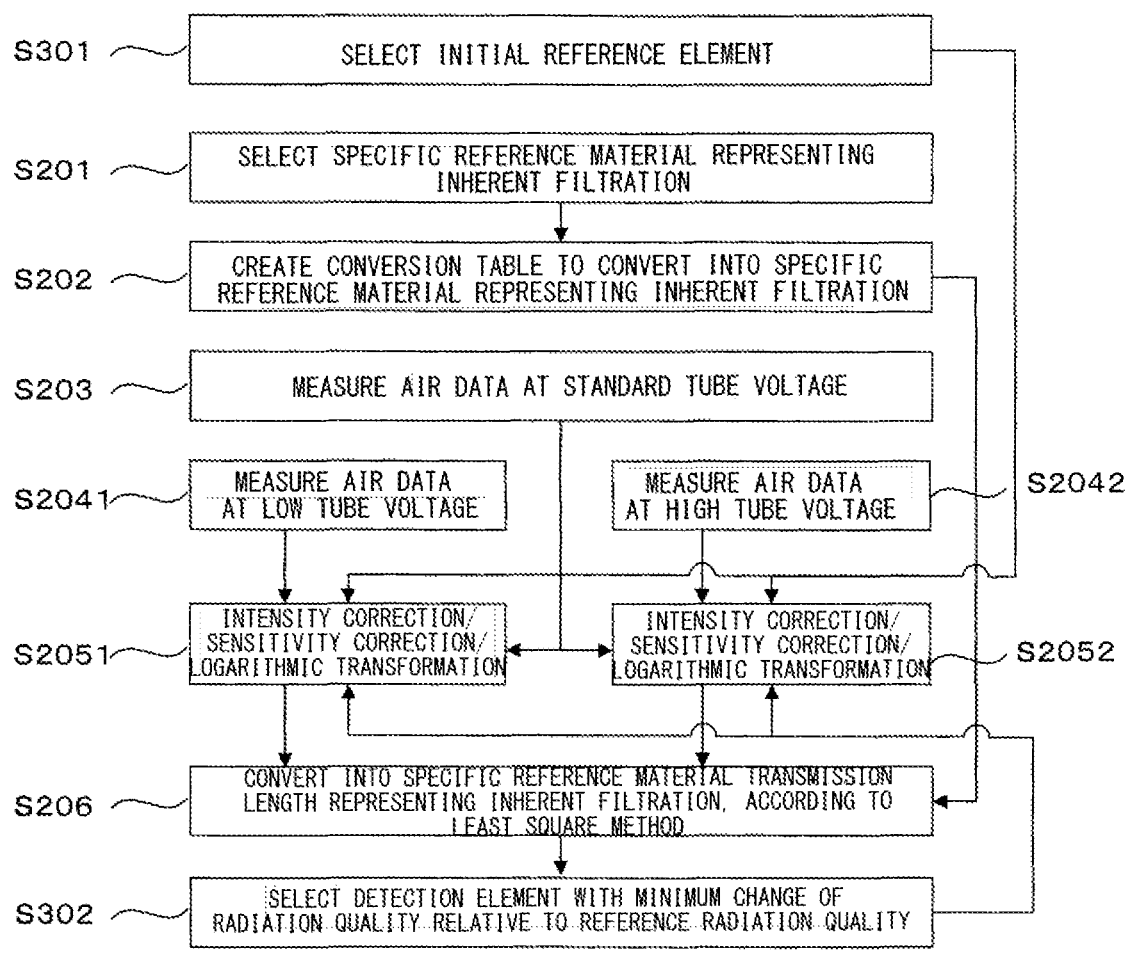
FIG. 5 illustrates a processing procedure according to a second embodiment.

With reference to the processing flowchart of FIG. 5, operations of the X-ray CT apparatus of the present embodiment having the aforementioned configuration will now be described. In FIG. 5, the process with a function being identical to the process in FIG. 4 is labeled with the same reference numeral, and they will not be redundantly explained, and only the different points will be focused in the following description.

Firstly, an initial reference element will be selected (S301). In the subsequent intensity correction process S2051 and S2052 of the air data measurement, the initial reference element is used for the aforementioned formulas 10 and 11. In the first embodiment, it has been described that an element with the minimum change of radiation quality should be preferably selected as the reference element. In the present embodiment, however, such reference element with the minimum change of radiation quality is estimated in the subsequent processing, and thus any appropriate element is selectable as the initial reference element in the process S301. Selection of the initial reference element may be performed by a user via the input unit 24, alternatively, a predetermined detection element may be provided by default.

Next, the same processes as the processes S201 to S206 of the first embodiment (FIG. 4) are performed, and inherent filtration, i.e., the transmission length of the specific reference material is obtained. Among the processes of S201 to S206, the processes S2051 and S2052 include the intensity correction using the reference element, and those processes are performed by the correction part 225. The transmission length of the specific reference material is obtained as to each detection element, and it may serve as an indicator of the change of radiation quality of each detection element.

A detection element with the least transmission length of the specific reference material, out of those transmission lengths obtained for the respective detection elements is considered as the detection element with the least change of radiation quality, and it is selected as the reference element (S302). The newly selected reference element is used in the intensity correction process S2051, S2052, and the transmission length conversion process S206, repeatedly, and thereafter a reference element is selected (S302). By repeating those processes S2051, S2052, S206, and S302, an element at which the change of radiation quality is minimum can be selected from the detector elements. It should be noted that the repeat count of the processes is not particularly limited. By way of example, it is possible to select an element as a final reference element, at the point when a difference between the specific reference material transmission length of the previously obtained reference element, and the specific reference material transmission length of the reference element currently obtained becomes equal to or less than a predetermined threshold.

As described so far, when the inherent filtration calculator 223 obtains the specific reference material transmission length, which is an indicator of the change of radiation quality, a detection element which is considered as having the least change of radiation quality is used as the reference element for the intensity correction of air data at each tube voltage, thereby enhancing the precision of the specific reference material transmission length being obtained.

In addition, there has been described to use a theoretical value of the X-ray energy spectrum $S(\varepsilon)$ in the formulas 1 and 3, when the image generator 221 creates the conversion table regarding the dependence on the transmission length of the reference material constituting the subject. It is further possible to measure an X-ray energy spectrum by a spectrometer at the position of the detection element selected in the process S302, and the measured spectrum may also be considered as the X-ray generation spectrum $S(\varepsilon)$ in the formulas 1 and 3. This may further enhance the precision of information such as the image being obtained accordingly.

Third Embodiment

The X-ray CT apparatus of the present embodiment is provided with a function to determine abnormality of a detection element or a detection module, by using inherent filtration as to each element calculated by the inherent filtration calculator.

In other words, the X-ray CT apparatus of the present embodiment is provided with a decision part 226 that determines abnormality of the detection element, according to the inherent filtration calculated by the inherent filtration calculator 223 as to each detection element. It may further be provided with a storage part 222 configured to record a result of the determination by the decision part 226. In addition, an alarm unit 227 may also be provided, which is configured to give warning when the decision part 226 decides abnormality.

The present embodiment also provides a monitoring method of the X-ray imaging apparatus that is provided with the X-ray detector having plural detection elements. According to this method, imaging is performed in advance by using different types of energy distributions in the state where no subject is placed, and plural types of air projection data are acquired. Then, from the plural types of air projection data, a change of radiation quality of the X-ray incident on each detection element, is calculated as a transmission length of any material (specific reference material), the number of which is equal to or less than the number of the types of energy distributions. Thereafter, by using thus calculated transmission length, a difference in a property of the radiation quality between the adjacent elements or between adjacent modules is displayed.

Figure 6:
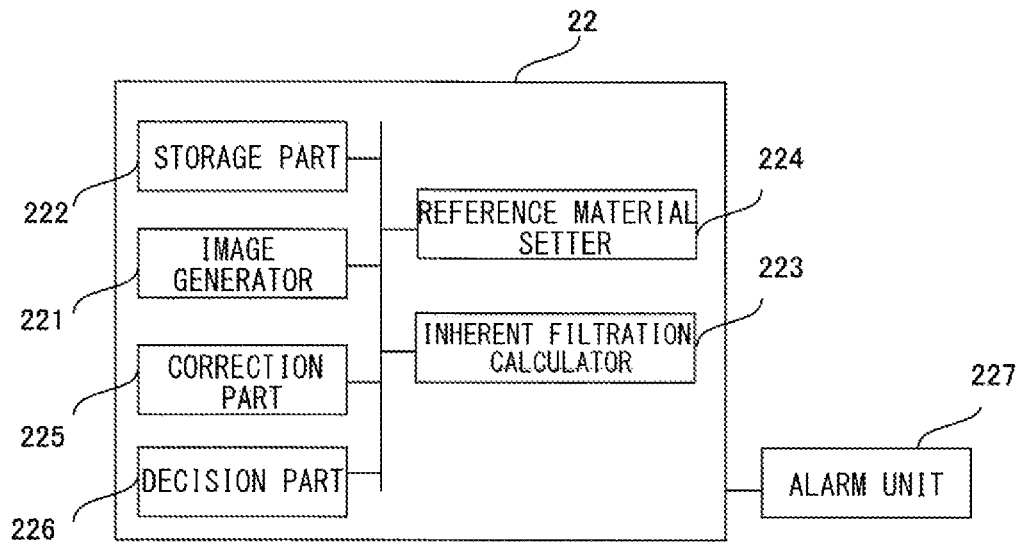
FIG. 6 is a functional block diagram showing the arithmetic unit according to a third embodiment.

FIG. 6 is a functional block diagram showing the X-ray CT apparatus (arithmetic unit 22) of the present embodiment. In FIG. 6, the elements identical to those in FIG. 2 are labeled with the same reference numerals and they will not be redundantly explained. As illustrated, the arithmetic unit 22 is provided with the image generator 221, the inherent filtration calculator 223, and the decision part 226. In addition, the X-ray CT apparatus is provided with the alarm unit 227 configured to give warning about a determination result of the decision part 226. It is alternatively possible that the output unit 25 (FIG. 1) is provided with the function of the alarm unit.

Figure 7:
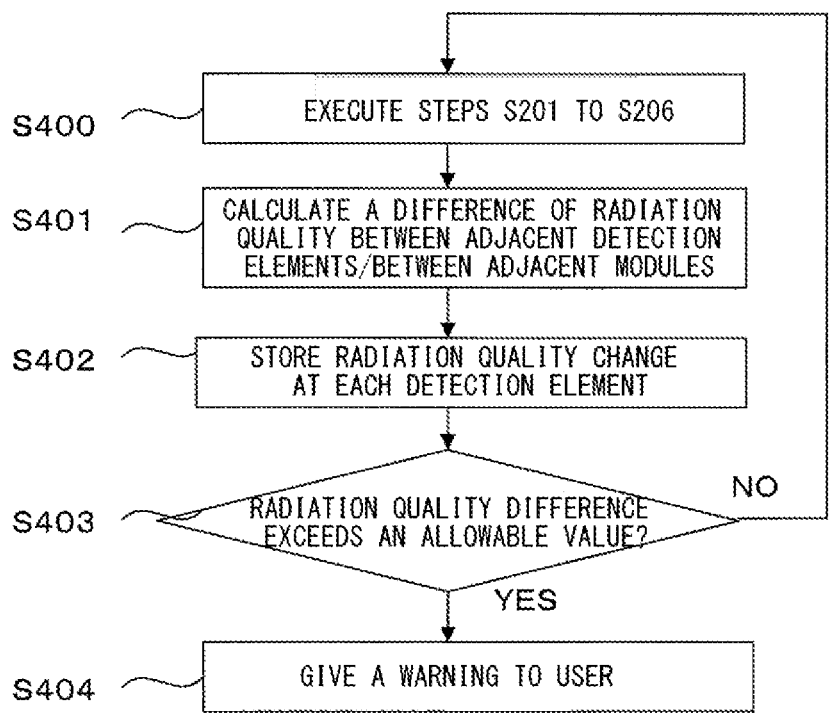
FIG. 7 illustrates a processing procedure according to the third embodiment.

With reference to the process flowchart of FIG. 7, processing mainly performed by the decision part 226 will now be described. Also in the X-ray CT apparatus of the present embodiment, a procedure of the inherent filtration calculator 223 to calculate the transmission length $s_j$ of the specific reference material, corresponding to the processes S201 to S206 as shown in FIG. 4, is collectively illustrated as a process 400, without providing redundant descriptions.

Firstly, a radiation quality difference $\Delta$ between the adjacent detection elements or a radiation quality difference $\Delta'$ between the detection modules is obtained (S401). The radiation quality difference $\Delta$ between the detection elements is defined according to the formula 14. The radiation quality difference $\Delta'$ between the detection modules is defined according to the formula 15.

[Formula 14]

$$\Delta=\Sigma_j\mu_j\rho_j(s_j(ch)-s_j(ch+1)) \quad (14)$$

where "ch" is a detection element number.

[Formula 15]

$$\Delta'=\Sigma_j\mu_j\rho_j(s'_j(mod)-s'_j(mod+1)) \quad (15)$$

where "mod" is a detection module number, and "$s'_j(mod)$" is an average of "$s_j$" within each detection module.

The value $\Delta$ or $\Delta'$ thus obtained is stored so as to record a change with passage of time (S402), and it is determined whether the value exceeds a predetermined threshold value (S403). As for the threshold value, an allowable change of radiation quality is obtained in advance within a range that has no effect on an image quality, and it can be used as the threshold. In the process S402, if the value $\Delta$ or $\Delta'$ exceeds the threshold value, it is determined that an abnormal radiation quality is found, and a user is notified of an alarm message via the alarm unit 227 (S404). Instead of notification to the user, or along therewith, the alarm message is displayed for a maintenance service person to provide the notification. Accordingly, the user or the personnel of the maintenance service is able to find the detection element or the detection module having a significantly different radiation quality, so that it takes measures such as replacement or rearrangement of the modules, and adjusting a beam compensation filter and a slice collimator.

The processes S400 to S403 may be performed on a regular basis, with recording a determination result of the decision part 226 accordingly. This allows recording of the radiation quality and its change with passage of time. It should be noted that since the air data of the apparatus is imaged on a regular basis, estimation of the inherent filtration may be performed concurrently therewith, automatically.

The X-ray imaging apparatus of the present invention has been described above, with describing the embodiments being applied to the X-ray CT apparatus. The present invention provides a method to estimate the inherent filtration caused by the apparatus, and it is applicable not only to the X-ray CT apparatus but also to another kind of X-ray imaging apparatus.

DESCRIPTION OF SYMBOLS

1 . . . X-ray tube (X-ray source), 2 . . . opening, 3 . . . subject, 4 . . . X-ray detector, 5 . . . scatter removal grid, 6 . . . bed, 7 . . . beam compensation filter, 8 . . . detector module, 9 . . . X-ray focused point, 10 . . . imaging part, 20 . . . operating part, 21 . . . recording unit, 22 . . . arithmetic unit, 23 . . . controller, 24 . . . input unit, 25 . . . output unit, 100 . . . the X-ray CT apparatus, 221 . . . image generator, 222 . . . storage part, 223 . . . inherent filtration calculator, 224 . . . reference material setter, 225 . . . correction part, 226 . . . decision part, 227 . . . alarm unit

What is claimed is:

1. An X-ray imaging apparatus comprising,
an X-ray source configured to generate plural X-rays having different energy,
an X-ray detector having plural detection elements and being disposed in a manner opposed to the X-ray source, and
a rotary plate configured to rotate with supporting the X-ray source and the X-ray detector, and
an arithmetic unit configured to calculate information as to a material existing between the X-ray source and the X-ray detector by using measured data detected by the X-ray detector under each of conditions of different X-ray energy distributions generated by the X-ray source, wherein,
the arithmetic unit comprises an inherent filtration calculator configured to use the measured data detected by the X-ray detector when no subject exists between the X-ray source and the X-ray detector, with respect to each of plural conditions of different X-ray energy distributions, so as to calculate a transmission length of an arbitrary reference material to obtain inherent filtration, as to each detection element of the X-ray detector.

2. The X-ray imaging apparatus according to claim 1, wherein,
the inherent filtration calculator creates a conversion table for converting an output from the X-ray detector into the transmission length of the reference material, and calculates the transmission length of the reference material, by using the conversion table, measured data detected by the X-ray detector, and a theoretical value of the output from the X-ray detector, the theoretical value being calculated for the reference material.

3. The X-ray imaging apparatus according to claim 1, wherein,
the inherent filtration calculator has a reference material setter configured to set the reference material.

4. The X-ray imaging apparatus according to claim 3, wherein,
the reference material setter sets as the reference material, a material being selected from those used to make a beam compensation filter.

5. The X-ray imaging apparatus according to claim 3, wherein,
the reference material setter sets as the reference material, a virtual material having a predetermined mass attenuation coefficient and a predetermined density.

6. The X-ray imaging apparatus according to claim 1, wherein,
the inherent filtration calculator uses the measured data obtained under two conditions; a low energy condition and a high energy condition, when no subject exists between the X-ray source and the X-ray detector, so as to calculate the transmission length of the reference material, the number of which is two or less.

7. The X-ray imaging apparatus according to claim 1, further comprising,
a storage part configured to store dependence of the X-ray detector output on a predetermined material constituting the subject, in the form of a subject transmission length conversion table, with respect to each of the conditions of different X-ray energy distributions, and
an image generator configured to use a measured value detected by the X-ray detector, when the subject exists between the X-ray source and the X-ray detector, with respect to each of the conditions of different X-ray energy distributions, a theoretical value calculated from the transmission length of the material constituting the subject, and the subject transmission length conversion table stored in the storage part, so as to create an image of the subject, wherein,
the subject transmission length conversion table is corrected by using the inherent filtration that is calculated by the inherent filtration calculator.

8. The X-ray imaging apparatus according to claim 7, wherein,
the image generator generates at least one of the following images; a material discrimination image for each of predetermined materials constituting the subject, a virtual standard tube voltage image, a virtual monochromatic image, an effective atomic number image, an electron density image, and an interaction intensified image.

9. The X-ray imaging apparatus according to claim 1, wherein,
the arithmetic unit comprises a decision part configured to determine abnormality of the detection element, according to the inherent filtration calculated by the inherent filtration calculator as to each detection element.

10. The X-ray imaging apparatus according to claim 9, further comprising a recording unit configured to record a determination result of the decision part.

11. The X-ray imaging apparatus according to claim 9, further comprising an output unit configured to output a determination result when the decision part determines abnormality.

12. The X-ray imaging apparatus according to claim 1, wherein,
the arithmetic unit comprises a correction part configured to perform intensity correction, using one of the plural detection elements as a reference element, wherein,
the arithmetic unit selects a detection element of which a change from a reference radiation quality is minimum, by using the transmission length of the reference material as to each detection element, calculated by the inherent filtration calculator, and the correction part performs the intensity correction using thus selected detection element as the reference element.

13. An X-ray imaging method of imaging a subject in different plural types of energy distributions and obtaining plural types of subject projection data, comprising,
imaging in advance without a subject in the different plural types of energy distributions,
calculating from air projection data obtained in the plural types of energy distributions, a change of radiation quality of X-rays incident on each detection element, as a transmission length of any material, the number of which is equal to or less than the number of the types of the energy distributions, and
producing an image where the change of radiation quality has been corrected, by using the change of radiation quality being calculated and the plural types of subject projection data.

14. The X-ray imaging method according to claim 13, wherein,
producing the image by using the plural types of subject projection data comprises,
a process of converting the plural types of subject projection data into transmission length data of plural types of materials constituting the subject, a process of correcting the transmission length data by using the change of the radiation quality being calculated, and a process of reconstructing the transmission length data being corrected to obtain an equivalent tomographic image of the materials constituting the subject.

15. A monitoring method of an X-ray imaging apparatus provided with an X-ray detector having plural detection elements, comprising, imaging in advance without any subject in different plural types of energy distributions, so as to obtain plural types of air projection data, calculating from the plural types of air projection data, a change of radiation quality of X-rays incident on each detection element, as a transmission length of any material, the number of which is equal to or less than the number of the types of the energy distributions, and displaying a difference of property of the radiation quality between the detection elements being adjacent or between modules being adjacent, by using the transmission length being calculated.

* * * * *